United States Patent [19]

Pfister et al.

[11] 4,180,662
[45] Dec. 25, 1979

[54] THIAZINE DERIVATIVES

[75] Inventors: Rudolf Pfister, Basel; Paul Zeller, Allschwil, both of Switzerland; Dieter Binder; Otto Hromatka, both of Vienna, Austria

[73] Assignee: Hoffmann-La Roche Inc., Nutley, N.J.

[21] Appl. No.: 938,274

[22] Filed: Aug. 31, 1978

[30] Foreign Application Priority Data

Sep. 6, 1977 [LU] Luxembourg .......................... 78083
Jul. 21, 1978 [CH] Switzerland ........................ 7908/78

[51] Int. Cl.$^2$ ............................................. C07D 513/04
[52] U.S. Cl. ............................................................. 544/48
[58] Field of Search ............................................. 544/48

[56] References Cited

U.S. PATENT DOCUMENTS

| | | | |
|---|---|---|---|
| 3,821,211 | 6/1974 | Sircar | 260/243 |
| 4,076,709 | 2/1978 | Hromatka et al. | 544/48 |
| 4,090,020 | 5/1978 | Binder et al. | 544/48 |

FOREIGN PATENT DOCUMENTS

| | | |
|---|---|---|
| 2232893 | 3/1976 | France . |
| 1308533 | 2/1973 | United Kingdom . |
| 1323283 | 7/1973 | United Kingdom . |
| 1519811 | 8/1978 | United Kingdom . |

*Primary Examiner*—John M. Ford
*Attorney, Agent, or Firm*—Jon S. Saxe; George M. Gould; Peter R. Shearer

[57] ABSTRACT

Anti-inflammatory, analgesic, anti-rheumatic and anti-thrombotic thienothiazine derivatives having the formula

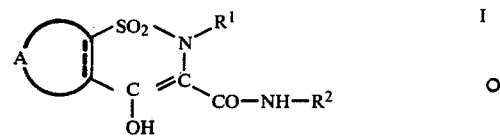

wherein A together with the two carbon atoms forms the group

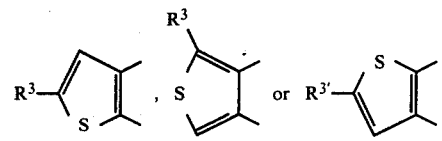

and the dotted line indicates the double bond present in the first and last thieno structures above, $R^1$ is lower alkyl, $R^2$ is the radical of an aromatic heterocycle with 1 to 4 hetero atoms optionally substituted by one or two lower alkyl groups, or a phenyl radical optionally substituted by halogen, hydroxy, lower alkyl, trifluoromethyl or lower alkoxy, $R^3$ is halogen and $R^{3'}$ is hydrogen or halogen, and pharmaceutically acceptable salts thereof are described.

17 Claims, No Drawings

THIAZINE DERIVATIVES

BRIEF SUMMARY OF THE INVENTION

The invention relates to compounds of the formula

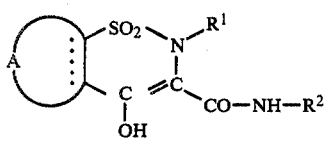

wherein A, $R^1$ and $R^2$ are as herein described, and pharmaceutically acceptable salts thereof which are useful as anti-inflammatory, analgesic, anti-rheumatic and anti-thrombotic agents.

In another aspect, the invention relates to a process for preparing the compounds of formula I.

DETAILED DESCRIPTION OF THE INVENTION

The invention relates to thiazine derivatives and more particularly thienothiazine derivatives of the formula

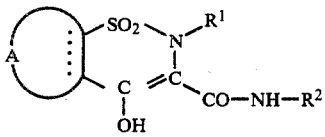

wherein A together with the two carbon atoms of the thiazine ring forms the group

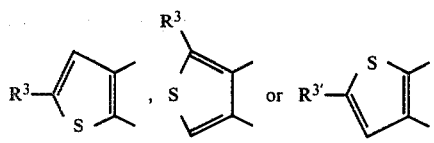

and the dotted line indicates the double bond present in the first and last thieno structures above, $R^1$ is lower alkyl, $R^2$ is the radical of an aromatic heterocycle with 1 to 4 hetero atoms optionally substituted by one or two lower alkyl groups, or is phenyl optionally substituted by halogen, hydroxy, lower alkyl, trifluoromethyl or lower alkoxy, $R^3$ is halogen and $R^{3'}$ is hydrogen or halogen, and to pharmaceutically acceptable salts thereof.

As used herein, the term "lower alkyl" denotes straight chain or branched saturated hydrocarbon groups with 1 to 4 carbon atoms, for example, methyl, ethyl, propyl, isopropyl, t-butyl and the like. The term "lower alkoxy" denotes hydrocarbonoxy groups with 1 to 4 carbon atoms. The term "halogen" refers to the four halogens, that is, chlorine, bromine, fluorine and iodine. The term "radical of an aromatic heterocycle with 1 to 4 carbon atoms optionally substituted by one or two lower alkyl groups" includes radicals of 5- or 6-membered aromatic heterocycles with 1 to 4 nitrogen and/or oxygen and/or sulfur atoms optionally substituted by one or two lower alkyl groups, for example, 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazine-3-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6-dimethyl-2-pyridyl, 5-isoxazolyl, 5-methyl-3-isoxazolyl, 3,4-dimethyl-5-isoxazolyl, 2,6-dimethyl-4-pyrimidinyl, 1,2,3,4-tetrazol-5-yl, and the like.

In a preferred class of compounds of formula I, $R^3$ and $R^{3'}$ are chlorine or bromine; chlorine is particularly preferred. $R^1$ is preferably methyl. $R^2$ preferably is 2-thiazolyl, 5-isoxazolyl or 2-pyridyl. A is preferably the group

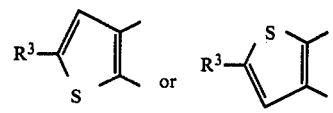

Particularly preferred compounds are 6-chloro-4-hydroxy-2-methyl-3-(2-pyridylcarbamoyl)-2H-thieno[2,3-e]-1,2-thiazine-1,1-dioxide and 6-chloro-4-hydroxy-2-methyl-3-(2-pyridyl-carbamoyl)-2H-thieno[3,2-e]-1,2-thiazine-1,1-dioxide.

The thienothiazine derivatives of formula I can be prepared in accordance with the invention by:

(a) reacting a compound of the formula

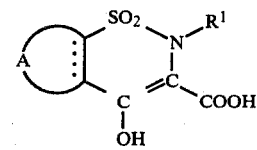

wherein R is lower alkyl and A, $R^1$, $R^3$ and $R^{3'}$ are as hereinbefore described,
with an amine of the formula $$H_2N\text{-}R^2 \qquad III$$

wherein $R^2$ is as hereinbefore described, or (b) cyclizing a reactive functional derivative of an acid of the formula

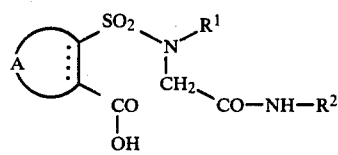

wherein A, $R^1$, $R^2$, $R^3$ and $R^{3'}$ are as hereinbefore described, or (c) lower alkylating a compound of the formula

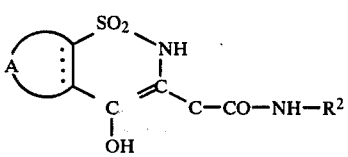

wherein A, $R^2$, $R^3$ and $R^{3'}$ are as hereinbefore described, or (d) reacting a compound of the formula

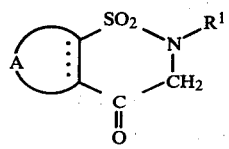

wherein A and $R^1$ are as hereinbefore described, with an isocyanate of the formula

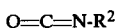

$$O=C=N-R^2 \qquad VII$$

wherein $R^2$ is as hereinbefore described,
and in the presence of a strong base, or
(e) hydrolyzing an enamine of the formula

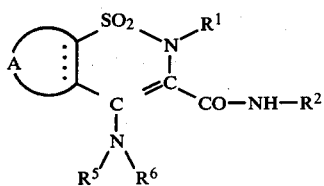

wherein A, $R^1$ and $R^2$ are as hereinbefore described, and $R^5$ and $R^6$ each is lower alkyl, or together with the nitrogen atom from pyrrolin-1-yl, pyrrolidin-1-yl, piperidino, morpholino or N-(lower alkyl)-piperazino, and (f) if desired, converting a resulting compound of formula I into a pharmaceutically acceptable salt.

The reaction according to process (a) can be carried out in the presence or absence of an inert solvent. Suitable solvents are alcohols, such as ethanol, or the like; hydrocarbons such as benzene, toluene, xylene, or the like; halogenated hydrocarbons such as chloroform, chlorobenzene, methylene chloride, carbon tetrachloride, or the like; dimethylformamide; or dioxane. The reaction is preferably carried out by heating, the melting point temperature or reflux temperature of the reaction mixture being particularly preferred.

In process (b), a reactive functional derivative of a compound of formula IV is cyclized. The cyclization is carried out in the presence of a base and preferably in the presence of a solvent at a temperature between 0° C. and the reflux temperature of the reaction mixture, preferably between room temperature and 60° C. Suitable bases are in particular hydrides, amides or alcoholates of alkali metals. Suitable solvents are aprotic and protic compounds, for example, alcohols such as methanol, ethanol; ethers such as dioxane; and acid amides such as dimethylformamide. The cyclization is conveniently carried out by dissolving the starting compound of formula IV in the solvent, adding the base, and allowing the reaction mixture to stand for 1 to 4 hours at room temperature or heating it to a temperature of up to 60° C. Particularly suitable reactive functional derivatives of the compounds of formula IV are their lower alkyl esters, for example, the methyl esters.

According to process (c), a compound of formula V is alkylated. The alkylation is conveniently carried out by dissolving the starting compound of formula V in an aprotic solvent, for example, acetonitrile, dioxane or dimethylformamide, converting it into the alkali metal salt by means of an alkali metal amide or hydride, and then converting it into the corresponding compound of formula I by treatment with an alkylating agent, in particular an alkyl halide or alkyl sulfate. The temperature and pressure for this process are not critical, and, accordingly, the reaction can be carried out at room temperature and atmospheric pressure for the sake of simplicity.

According to process (d), a compound of formula VI is reacted with an isocyanate of formula VII in the presence of a strong base. Suitable strong bases are alkali metal amides, alkali metal or alkaline earth metal hydrides, as well as metal alkalis or alkaline earths. The reaction is preferably carried out under an inert gas, for example, nitrogen, at a temperature between 0° C. and 50° C., preferably at room temperature, and in the presence of an inert, polar solvent, for example, toluene, dioxane, dimethylformamide, dimethylsulfoxide or hexamethyl phosphoric acid triamide (HMTP). The isocyanates of formula VII required as starting substances are either known or can be synthesized in a manner similar to the preparation of the known compounds.

According to process (e), an enamine of formula VIII is hydrolyzed. The hydrolysis is preferably carried out with an aqueous mineral acid, for example, hydrochloric acid, hydrobromic acid, hydroiodic acid, sulfuric acid, or with trifluoroacetic acid, at a temperature between 50° C. and the boiling point of the reaction mixture; preferably the boiling point of the reaction mixture is employed. In this hydrolysis, the acid also acts as a solvent.

The starting compounds for process variant (a) can be prepared in a manner known starting from known products. In particular, they can be synthesized according to the following reaction schemes and according to the specific details given in the Examples. Reaction Scheme I refers to compounds wherein A is

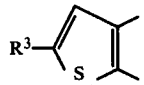

Reaction Scheme II refers to compounds wherein A is

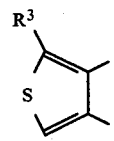

and Reaction Scheme III refers to compounds wherein A is

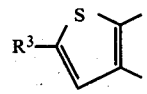

Reaction Scheme I

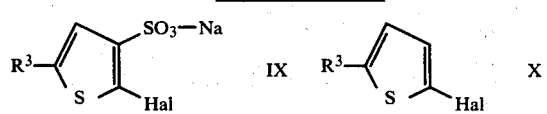

4,180,662
-continued
Reaction Scheme I
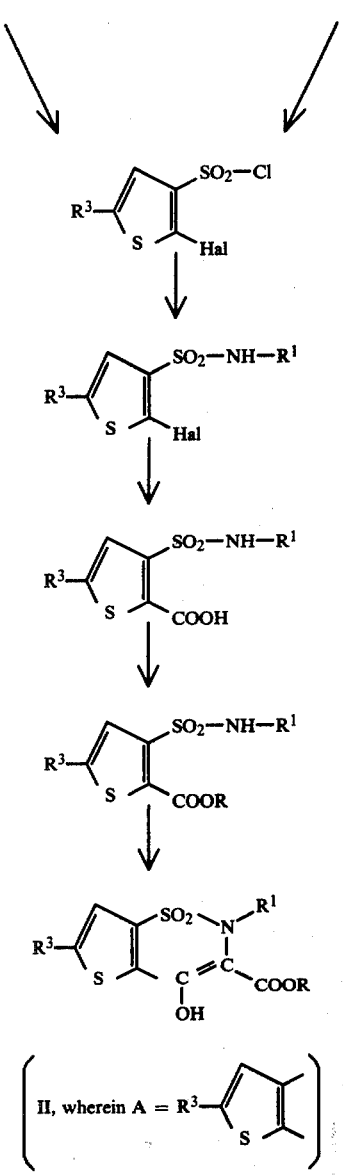
(II, wherein $A = \underset{R^3}{\overset{}{\underset{S}{\bigcirc}}}$)
Reaction Scheme II
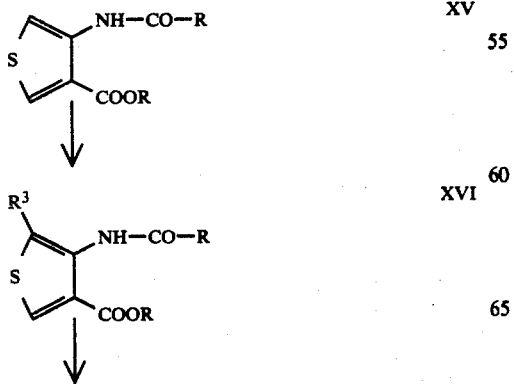
-continued
Reaction Scheme II
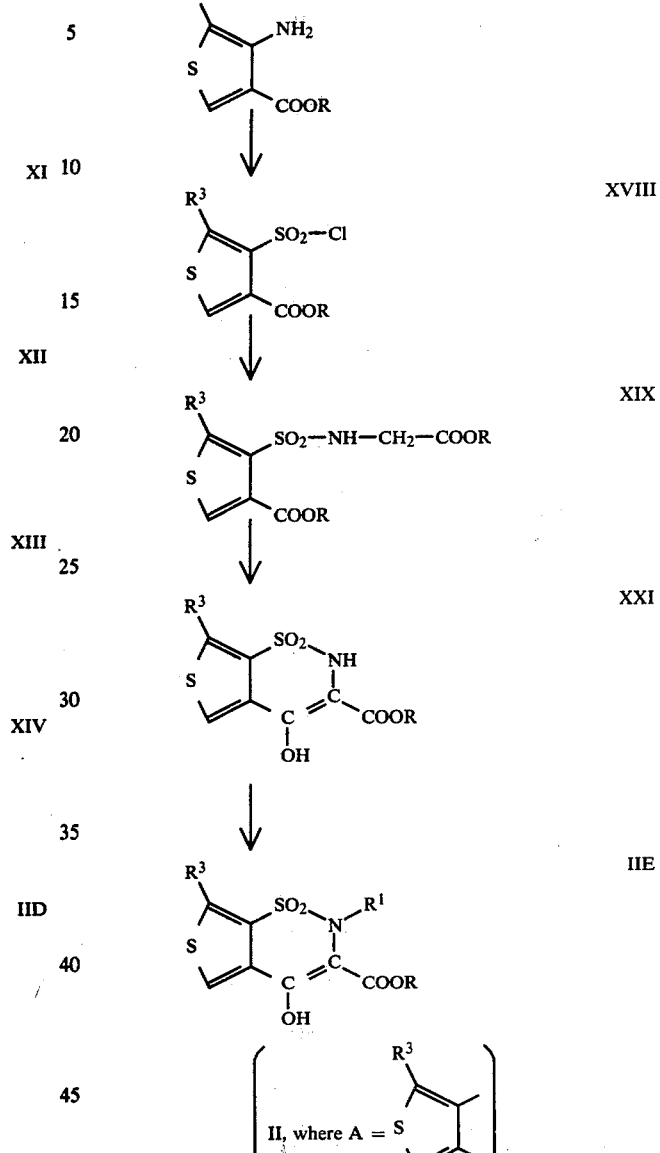
(II, where $A = \underset{S}{\overset{R^3}{\bigcirc}}$)
Reaction Scheme III
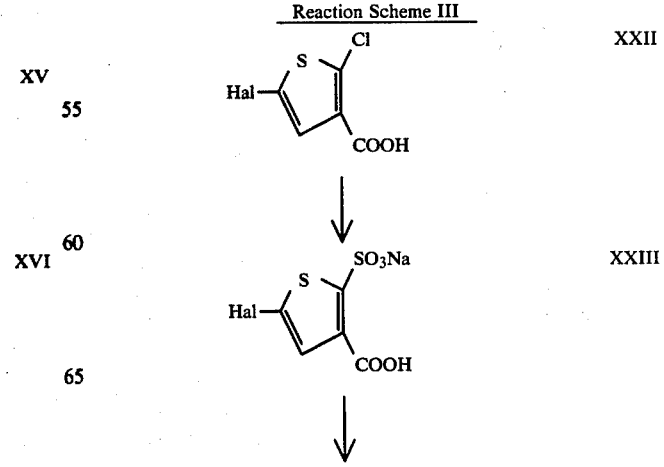

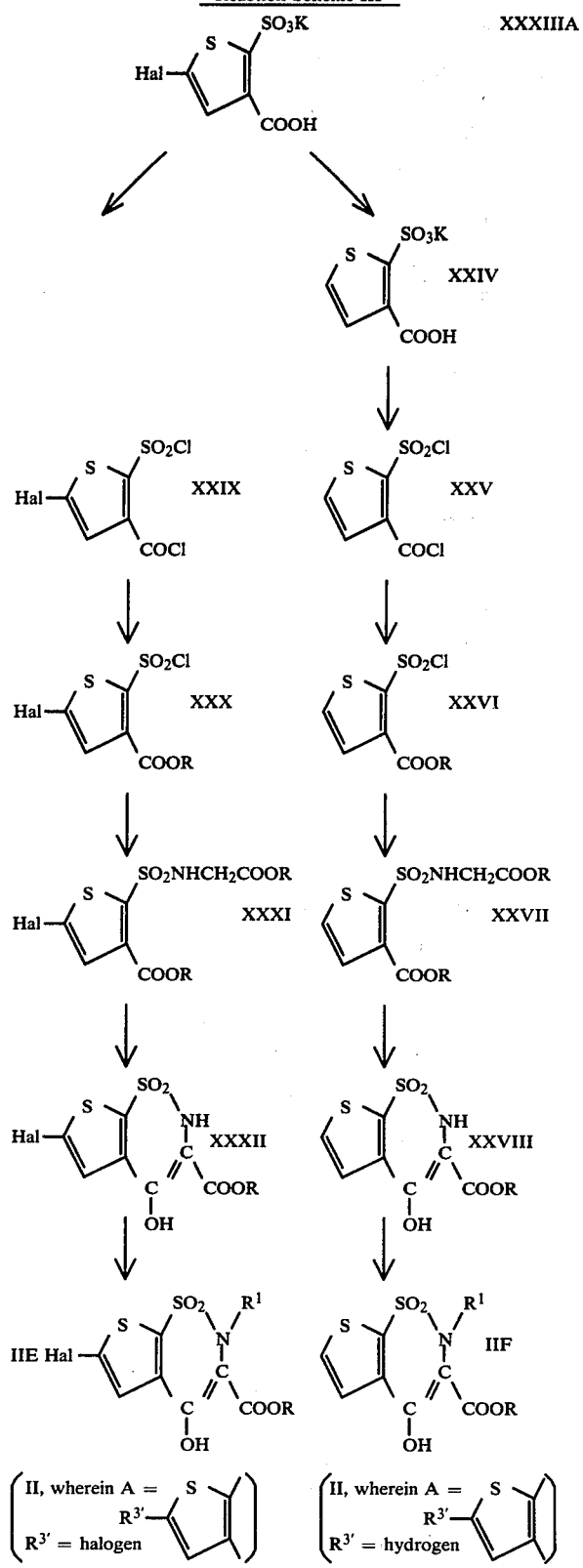

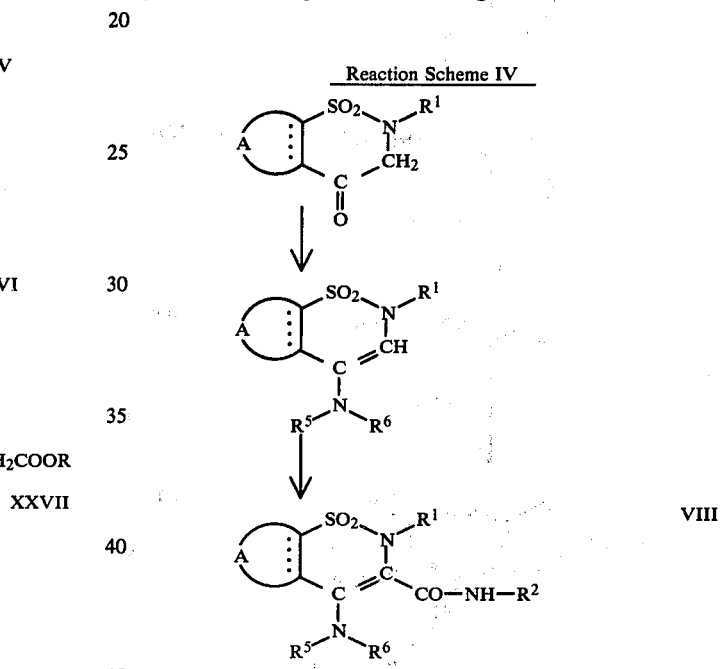

formula III with chloracetyl chloride and reacting the product obtained of the formula $$R^2-NH-\overset{\underset{\|}{O}}{C}-CH_2-Cl$$

wherein $R^2$ is as hereinbefore described,
with a compound of formula XIV. Other reactive functional derivatives of the acid of formula IV can be prepared in a known manner from the esters obtained.

For process (c), the starting compounds of formula V that can be used may for example be obtained by reacting a compound of formula XXI, XXVIII or XXXII with an amine of formula III.

The starting substances of formula VI required for process (d) can be prepared by known methods.

The starting substances for process (e) can be prepared according to the following Reaction Scheme IV.

The compounds of formula I can form pharmaceutically acceptable salts with corresponding bases. Suitable bases are alkali metals (e.g. lithium, sodium, potassium), alkaline earth metals (e.g. magnesium and calcium) and amines (e.g. triethanolamine, diethylaminoethanol, triethylamine, trimethylamine, diethylamine and the like). Compounds of formula I which contain a basic heterocyclic radical $R^2$ can also form pharmaceutically acceptable acid addition salts with strong acids, in particular with mineral acids (e.g. hydrochloric acid).

The compounds of formula I and their pharmaceutically acceptable salts have an anti-inflammatory, analgesic, and anti-rheumatic effect. These valuable pharmacological properties can be demonstrated utilizing standard methods, for example, by the known kaolin paw edema test (in rats). In this test, an acute local inflammation is produced in the right hind paw of a rat by intradermal injection of 0.1 ml. of a 10% kaolin suspension (bolus alba). The substance to be investigated is administered orally, and the following parameters are measured:

1. Diameter of the paw in mm (as an indication of the severity of the inflammation);

2. Pressure (in g.) on the paw (to determine the pain threshold).

The substance being investigated is administered ½ hour before and 3½ hours after the kaolin injection, and the aforementioned parameters are measured 4 hours after the said kaolin injection. The edema-inhibiting effect is given as a percentage based on the difference in the edema intensity between untreated animals and animals treated with the substance being investigated, and the anti-nociceptive activity is given as the percentage increase in the pain threshold.

In this test, 6-chloro-4-hydroxy-2-methyl-3-(pyridylcarbamoyl)-2H-thieno[2,3-e]-1,2-thiazine-1,1-dioxide at a dosage of 0.3 mg/kg. orally produces a 20% edema inhibition and a 97% increase in the pain threshold, and at a dosage of 1 mg/kg. orally produces a 33% edema inhibition and a 129% increase in the pain threshold.

The compounds of formula I have qualitatively a similar effect to that of phenylbutazone, which is well known for its therapeutic use and properties. Also, they inhibit blood platelet aggregation—as can be shown by the appropriate standard test—and therefore also have anti-thrombotic properties.

The compounds of formula I and their pharmaceutically acceptable salts can be used as medicaments, for example, in the form of pharmaceutical preparations containing the said compounds mixed with a pharmaceutical organic or inorganic inert carrier suitable for enteral or parenteral application, for example, water, gelatin, gum arabic, lactose, starch, magnesium stearate, talc, vegetable oils, polyalkylene glycols, or the like. The pharmaceutical preparations may be formulated in solid form, for example, as tablets, dragees, suppositories, capsules, in semi-solid form, for example, as ointments, or in liquid form, for example, as solutions, suspensions or emulsions. If necessary, they can be sterilized and/or contain adjuvants such as preservatives, stabilizing agents or emulsifying agents, salts for altering the osmotic pressure, or buffers. They can also contain other therapeutically valuable substances.

The compounds of formula I can be administered orally to humans in a daily dosage of 1–100 mg., preferably 2–10 mg.

The Examples which follow, in which all temperatures are given in degrees Centigrade, further illustrate the invention.

EXAMPLE 1

Preparation of 4-hydroxy-2-methyl-3-(2-pyridylcarbamoyl)-2H-thieno[3,2-e]-1,2-thiazine-1,1-dioxide 4.2 g. of 4-hydroxy-2-methyl-3-methoxycarbonyl-2H-thieno[3,2-e]thiazine-1,1-dioxide are heated for 18 hours under reflux with 2.15 g. of 2-aminopyridine in 220 ml. of absolute xylene, while passing a stream of nitrogen through the reaction mixture, following which the mixture is cooled to room temperature. Crystallization of the product is initiated by scratching. After keeping the reaction mixture overnight in the cold, the precipitated product is suction filtered, digested with a small amount of dioxane, and recrystallized from ethanol, and 4-hydroxy-2-methyl-3-(2-pyridylcarbamoyl)-2H-thieno[3,2-e]-1,2-thiazine-1,1-dioxide having a melting point of 223°–225° (with decomposition) is obtained.

The starting product used in this Example is obtained as follows:

59 g. of sodium hydroxide are dissolved in 637 ml. of water. The solution is heated to 90°, and 290.7 g. of 2,5-dichlorothiophene-3-carboxylic acid are added and dissolved by stirring. 156 g. of sodium hydrogen sulfite dissolved in 430 ml. of water is added to the solution and the pH thereof is adjusted to 7.5–7.7 with approximately 167 ml. of 30% caustic soda. 12 g. of finely powdered cuprous chloride are added to the clear solution, which is then boiled for 24 hours under reflux. The solution is filtered hot from the copper oxide and the filtrate is acidified with 400 ml. of concentrated HCl and cooled to 5°. The precipitate that has separated out is suction filtered without rewashing and dried in vacuo at 110° to constant weight. The precipitate is then boiled up with 3×500 ml. portions of methylene chloride. The residue is dried at 70° in vacuo, and sodium 5-chloro-2-sulfothiophene-3-carboxylate is obtained.

129 g. of sodium 5-chloro-2-sulfothiophene-3-carboxylate are dissolved hot in a solution of 84.7 g. of caustic potash in 430 ml. of water, acidified with 130 ml. of concentrated HCl to a pH of 1, and slowly cooled to 5°. The precipitate that separates out is suction filtered without rewashing. The filtrate is concentrated by evaporation to 220 ml. and again cooled to 5°. The precipitate that separates out is suction filtered, combined with the previously obtained product, and dried in vacuo at 110°. Potassium 5-chloro-2-sulfothiophene-3-carboxylate is obtained.

40 g. of potassium 5-chloro-2-sulfothiophene-3-carboxylate are dissolved in 24 g. of caustic potash dissolved in 400 ml. of water, stirred with 4 g. of activated charcoal, and filtered. 2 g. of palladium/activated charcoal (10% Pd) are then added and the mixture is hydrogenated at room temperature and at an initial pressure of approximately 1 atmosphere until no more hydrogen is taken up. The catalyst is removed by filtration. The filtrate is concentrated by evaporation to 35 ml., and acidified with concentrated HCl to a pH of 1. The precipitate that separates out is redissolved by heating. The resulting solution is cooled to 5°, and the precipitated product is suction filtered without rewashing and dried in vacuo to constant weight, and potassium 2-sulfothiophene-3-carboxylate is obtained.

64 g. of potassium 2-sulfothiophene-3-carboxylate are suspended in 260 ml. of phosphorus oxychloride. 114 g. of phosphorus pentachloride are added to the suspension, which is then heated for 3 hours at 95°. The suspension is then cooled to 10°. The precipitated inorganic salts are separated by suction filtration. The filtrate is concentrated by evaporation in vacuo as far as possible, and the residue is then taken up in 500 ml. of absolute chloroform to remove inorganic salts still present, and is then filtered. After evaporation of the solvent, an oily residue remains which does not crystallize but is sufficiently pure for the further reaction. 2-chlorosulfonylthiophene-3-carboxylic acid chloride is obtained.

51 g. of 2-chlorosulfonylthiophene-3-carboxylic acid chloride are dissolved in 510 ml. of absolute chloroform, 10 g. of absolute methanol is added, and the mixture is boiled under reflux until no further HCl is evolved (about 4 hours). The oil remaining after distilling of the solvent crystallizes on cooling and is used as such in the next stage. Methyl 2-chlorosulfonylthiophene-3-carboxylate having a melting point of 51°–54° is obtained.

47.5 g. of methyl-2-chlorosulfonylthiophene-3-carboxylate and 49.7 of glycinemethylester hydrochloride are stirred in 475 ml. of absolute pyridine for 6 hours at room temperature. The solvent is then distilled in vacuo. The residue is distributed between 300 ml. of 2 N HCl and 1 liter of ether. The organic phase is separated and the aqueous phase is extracted by shaking with 4×250 ml. of ether. The combined organic phases are dried with sodium sulfate, stirred with activated charcoal, filtered and concentrated by evaporation. The oily residue crystallizes on cooling, and methyl 2-(N-methoxycarbonylmethyl)-sulfamoylthiophene-3-carboxylate having a melting point of 120°–124° is obtained.

5.7 g. of sodium are dissolved in 150 ml. of absolute methanol, concentrated to dryness by evaporation in vacuo, and then heated in vacuo for 1 hour at 100°. 30.2 g. of methyl 2-(N-methoxycarbonylmethyl)-sulfamoyl-thiophene-3-carboxylate are dissolved in 250 ml. of absolute benzene while heating, added to the solution of the above-prepared sodium methylate suspended in 52 ml. of absolute benzene, and stirred at 60° for 4 hours under nitrogen. The mixture is then poured onto 350 ml. of 2 N HCl and 200 g. of ice, while stirring, and extracted with 3×300 ml. of methylene chloride. The combined organic phases are extracted by shaking with 3×250 ml. of 10% sodium acetate solution, the aqueous phases in each case being reshaken with a small amount of methylene chloride. The combined organic phases are extracted with 5×200 ml. of 10% sodium carbonate solution. The resulting aqueous phase is in each case reshaken with a small amount of methylene chloride. The combined aqueous phases are acidified with concentrated HCl to a pH of 1. The precipitated product is extracted with 3×500 ml. of methylene chloride. The combined organic phases are dried with sodium sulfate, stirred with activated charcoal, filtered, and concentrated by evaporation, whereupon the product crystallizes out, and 4-hydroxy-3-methoxycarbonyl-2H-thieno[3,2-e]-1,2-thiazine-1,1-dioxide having a melting point of 210°–212° (with decomposition) is obtained.

8.0 g. of 4-hydroxy-3-methoxycarbonyl-2H-thieno[3,2-e]-1,2-thiazine-1,1-dioxide are dissolved in 80 ml. of absolute dimethylformamide and cooled to 0°. 2.7 g. of 58% sodium hydride suspension in mineral oil, which has been freed from oil by washing with 2×20 ml. of absolute benzene, is then added and the mixture is stirred for 2 hours at 0°. 4.8 g. of methyl iodide are then added in such a manner that the temperature does not rise above 10°. After the end of the addition, the mixture is stirred for 2 hours at room temperature. The solvent is distilled in a water jet vacuum and the residue is distributed between 100 ml. of 2 N HCl and 400 ml. of methylene chloride. The organic phase is separated and shaken again with 2×100 ml. of methylene chloride. The combined organic phases are dried with sodium sulfate, stirred with activated charcoal, filtered, and the solvent is distilled. The oily residue is crystallized with methanol, the crystalline product is removed by filtration under suction and digested with a small amount of ice-cold methanol, whereby 4-hydroxy-2-methyl-3-methoxycarbonyl-2H-thieno[3,2-e]1,2-thiazine-1,1-dioxide having a melting point of 178°–180° is obtained.

EXAMPLE 2

Preparation of 4-hydroxy-2-methyl-3-(2-thiazolylcarbamoyl)-2H-thieno[3,2-e]1,2-thiazine-1,1-dioxide 0.25 g. of 4-hydroxy-2-methyl-3-methoxycarbonyl-2H-thieno[3,2-e]1,2-thiazine-1,1-dioxide is heated under reflux for 17 hours with 0.14 g. of 2-aminothiazole in 28 ml. of absolute xylene, while passing a stream of nitrogen through the said mixture. The mixture is cooled to room temperature and crystallization of the product is initiated by scratching. The product is kept overnight in the cold. The precipitate crystals are removed by filtration under suction and recrystallized from ethanol, whereby 4-hydroxy-2-methyl-3-(2-thiazolylcarbamoyl)-2H-thieno[3,2-e]1,2-thiazine-1,1-dioxide having a melting point of 226°–227° (with decomposition) is obtained.

EXAMPLE 3

Preparation of 4-hydroxy-2-methyl-3-pyrazinylcarbamoyl-2H-thieno[3,2-e]1,2-thiazine-1,1-dioxide 0.25 g. of 4-hydroxy-2-methyl-2-methoxycarbonyl-2H-thieno[3,2-e]1,2-thiazine-1,1-dioxide is heated under reflux for 22 hours with 0.13 g. of aminopyrazine in 28 ml. of absolute xylene, while passing a stream of nitrogen through the mixture. The reaction mixture is kept overnight in the cold and the precipitated product is filtered under suction and digested with a small amount of dioxane. The product is then recrystallized from ethanol, and 4-hydroxy-2-methyl-3-pyrazinylcarbamoyl-2H-thieno[3,2-e]1,2-thiazine-1,1-dioxide having a melting point of 246°–247° (with decomposition) is obtained.

EXAMPLE 4

Preparation of 4-hydroxy-2-methyl-3-[3-(5-methylisoxazolyl)-carbamoyl]-2H-thieno[3,2-e]1,2-thiazine-1,1-dioxide 0.25 g. of 4-hydroxy-2-methyl-3-methoxycarbonyl-2H-thieno[3,2-e]1,2-thiazine-1,1-dioxide is heated under reflux for 14 hours with 0.13 g. of 3-amino-5-methylisoxazole in 28 ml. of absolute xylene, while passing a stream of nitrogen through the mixture. The mixture is allowed to cool to room temperature and the product is crystallized by scratching. The reaction mixture is kept overnight in the cold and the precipitated product is filtered under suction and recrystallized from ethanol, and 4-hydroxy-2-methyl-3-[3-(5-methylisoxazolyl)-carbamoyl]-2H-thieno[3,2-e]1,2-thiazine-1,1-dioxide having a melting point of 243°–244° (with decomposition) is obtained.

EXAMPLE 5

Preparation of 6-chloro-4-hydroxy-2-methyl-3-(2-pyridylcarbamoyl)-2H-thieno[3,2-e]1,2-thiazine-1,1-dioxide 0.4 g. of 6-chloro-4-hydroxy-2-methyl-3-methoxycarbonyl-2H-thieno[3,2-e]1,2-thiazine-1,1-dioxide and 0.18 g. of 2-aminopyridine are refluxed in 45 ml. of absolute xylene for 16 hours while passing a stream of nitrogen through the mixture. The reaction mixture is allowed to cool to room temperature and the product is crystallized by scratching. The reaction mixture is kept overnight in the cold. The precipitated crystals are filtered under suction, recrystallized from dioxane, and 6-chloro-4-hydroxy-2-methyl-3-(2-pyridylcarbamoyl)-2H-thieno[3,2-e]1,2-thiazine-1,1-dioxide having a melting point of 239°–241° (with decomposition) is obtained.

The starting material used in this Example is obtained as follows:

25 g. of potassium 5-chloro-2-sulfothiophene-3-carboxylate are suspended in 100 ml. of phosphorus oxychloride while stirring. 39 g. of phosphorus pentachloride are added to the suspension, and the mixture is then stirred for 3 hours at 95°. Thereafter, the mixture is cooled to 10° and separated from precipitated inorganic salts by suction filtration. The filtrate is concentrated by evaporation in vacuo as far as possible and then taken up in 200 ml. of absolute chloroform to remove inorganic salts still present, and is finally filtered. The solvent is distilled to leave a non-crystallizing oil, and 5-chloro-2-chlorosulfonylthiophene-3-carbxoylic acid chloride is obtained.

21 g. of 5-chloro-2-chlorosulfonylthiophene-3-carboxylic acid chloride are dissolved in 210 ml. of absolute chloroform, 3.6 g. of absolute methanol are added, and the mixture is boiled under reflux (approximately 4 hours) until no more HCl is evolved. The solvent is distilled to leave an oil that crystallizes out on cooling, which latter can be worked up without further purification, and methyl 5-chloro-2-chlorosulfonylthiophene-3-carboxylate is obtained.

18.6 g. of methyl 5-chloro-2-chlorosulfonylthiophene-3-carboxylate and 17 g. of glycine-methylester hydrochloride are stirred in 190 ml. of absolute pyridine for 6 hours at room temperature. The solvent is then distilled in vacuo. The residue is distributed between 150 ml. of 2 N HCl and 400 ml. of ether, the organic phase is separated, and the aqueous phase is extracted by shaking with 3×100 ml. of ether. The combined organic phases are dried over sodium sulfate, stirred with activated charcoal, filtered, and concentrated by evaporation. The oily residue is crytallized with ether, filtered under suction, digested with a small amount of ice-cold ether, and methyl-5-chloro-2-(N-methoxycarbonylmethyl)-sulfamoylthiophene-3-carboxylate having a melting point of 95°-97° is obtained.

10.6 g. of sodium are dissolved in 100 ml. of absolute methanol. The solution is concentrated by evaporation in vacuo and then heated for 1 hour at 100° in vacuo. 10.6 g. of methyl 5-chloro-2-(N-methoxycarbonylmethyl)-sulfamoylthiophene-3-carboxylate are dissolved in 75 ml. of absolute benzene, and the sodium methylate prepared above and suspended in 33 ml. of absolute benzene is added to this solution and stirred for 6 hours at 60°. The mixture is then poured onto 150 ml. of 2 N HCl and 100 g. of ice and extracted by shaking with 3×200 ml. of methylene chloride. The combined organic phases are extracted by shaking with 3×100 ml. of 10% sodium acetate solution, the aqueous phases in each case being reshaken with a small amount of methylene chloride. The organic phases are then extracted with 5×150 ml. of 10% sodium carbonate solution, the aqueous phases in each case being reshaken with a small amount of methylene chloride. The combined aqueous phases are acidified to pH 1 with concentrated HCl, and the product that precipitates out is extracted with 3×200 ml. of methylene chloride. The combined organic phases are dried with sodium sulfate, stirred with activated charcoal, filtered, and concentrated by evaporation, whereupon the product crystallizes out and 6-chloro-4-hydroxy-3-methoxycarbonyl-2H-thieno[3,2-e]-1,2-thiazine-1,1-dioxide having a melting point of 178°-179° is obtained.

1.9 g. of 6-chloro-4-hydroxy-3-methoxycarbonyl-2H-thieno[3,2-e]1,2-thiazine-1,1-dioxide is dissolved in 19 ml. of absolute dimethylformamide and cooled to 0°. 0.56 g. of a sodium hydride suspension in 58% mineral oil, which has been freed from oil by washing with 2×10 ml. of absolute benzene, is then added and the mixture is stirred at 0° for 2 hours. 1.0 g. of methyl iodide is then added in such a manner that the temperature does not exceed 10°. Thereafter, the mixture is stirred for 2 hours at room temperature. The solvent is distilled in vacuo and the residue is distributed between 100 ml. of 2 N HCl and 200 ml. of methylene chloride. The phases are separated and the aqueous phase is extracted by shaking with 50 ml. of methylene chloride. The combined organic phases are dried with sodium sulfate, stirred with activated charcoal, filtered, and concentrated by evaporation. The remaining oil is crystallized with methanol. The product is filtered under suction and digested with a small amount of methanol, and 6-chloro-4-hydroxy-2-methyl-3-methoxycarbonyl-2H-thieno[3,2-e]1,2-thiazine-1,1-dioxide having a melting point of 173°-174° is obtained.

EXAMPLE 6

Preparation of
6-chloro-4-hydroxy-2-methyl-3-(2-thiazolylcarbamoyl)-2H-thieno[3,2-e]-1,2-thiazine-1,1-dioxide 0.4 g. of 6-chloro-4-hydroxy-2-methyl-3-methoxycarbonyl-2H-thieno[3,2-e]1,2-thiazine-1,1-dioxide is heated under reflux for 16 hours with 0.19 g. of 2-aminothiazole in 45 ml. of absolute xylene, while passing a stream of nitrogen through the mixture. The reaction mixture is cooled to room temperature, and the product is crystallized out by scratching and then kept overnight in the cold. The precipitate crystals are removed by filtration under suction, recrystallized from ethanol, and 6-chloro-4-hydroxy-2-methyl-3-(2-thiazolecarbamoyl)-2H-thieno[3,2-e]1,2-thiazine-1,1-dioxide having a melting point of 136°-138° (with decomposition) is obtained.

EXAMPLE 7

Preparation of
6-chloro-4-hydroxy-2-methyl-3-(2-pyridylcarbamoyl)-2H-thieno[3,2-e]1,2-thiazine-1,1-dioxide 2.59 g. of 6-chloro-3,4-dihydro-2-methyl-4-oxo-2H-thieno[3,2-e]-thiazine-1,1-dioxide and 1.8 ml. of pyrrolidine are dissolved in 20 ml. of benzene. 3 mg. of p-toluenesulfonic acid monohydrate is added and the mixture is then heated under reflux on a water separator until 0.2 ml. of water has collected. The mixture is evaporated to dryness, dried in a high vacuum, and the residue is taken up in a small amount of benzene and diluted with diethyl ether and hexane. Cubic, red-brown crystals of 6-chloro-2-methyl-4-(1-pyrrolidino)-2H-thieno[3,2-e]1,2-thiazine-1,1-dioxide having a melting point of 150°-151.5° crystallize out at −25°.

A solution of 1.34 g. of 6-chloro-2-methyl-4-(1-pyrrolidino)-2H-thieno[3,2-e]1,2-thiazine-1,1-dioxide and 0.8 ml. of triethylamine in 25 ml. of a 4:1 mixture of tetrahydrofuran and benzene is added dropwise during 1 hour to a stirred mixture of 0.5 g. phosgene, 6 ml. of benzene and 3 ml. of tetrahydrofuran cooled to −10°. The reaction mixture is allowed to stand for 15 hours at −25°, is heated to 20°, and a solution of 0.64 g. of 2-aminopyridine and 0.8 ml. of triethylamine in 5 ml. of tetrahydrofuran is added dropwise during 30 minutes, while stirring. The reaction mixture is heated for an additional 2 hours under reflux, poured onto ice water, extracted with methylene chloride, the organic phase is evaporated to dryness, and the residue is chromatographed on silica gel. The column is eluted with methylene chloride-ethylacetate 9:1, and 6-chloro-2-methyl-3-(2-pyridylcarbamoyl)-4-(1-pyrrolidino)-2H-thieno[3,2- e]-thiazine-1,1-dioxide crystallizes, after concentration by evaporation, from diethyl ether in the form of yellow hexagonal crystals having a melting point of 167.5°–168°.

0.5 g. of 6-chloro-2-methyl-3-(2-pyridylcarbamoyl)-4-(1-pyrrolidino)-2H-thieno-[3,2-e]1,2-thiazine-1,1-dioxide is heated under reflux for 15 minutes in 15 ml. of 2 N hydrochloric acid. Most of the hydrochloric acid is removed in vacuo, and the residue is taken up in phosphate buffer solution of pH 6 and extracted several times with methylene chloride. The solvent is removed in vacuo. The solid yellow residue is recrystallized from dioxane and 6-chloro-4-hydroxy-2-methyl-3-(2-pyridylcarbamoyl)2H-thieno[3,2-e]1,2-thiazine-1,1-dioxide is obtained as a yellow crystalline powder having a melting point of 238°–239°.

EXAMPLE 8

Preparation of methyl 5-chloro-3-methylsulfamoylthiophene-2-carboxylate

A mixture of 1230 g. of chlorosulfonic acid and 100 g. of thionyl chloride is placed in a 4 l. volume flask and cooled to 5° by means of an ice bath. 647 g. of 2,5-dichlorothiophene is then carefully added slowly so that the temperature of the reaction mixture does not exceed 7°. A vigorous evolution of gas takes place. After the end of the addition, the reaction solution is stirred for an additional 1½ hours at 15°. The slightly reddish solution obtained is then carefully poured onto ice. The mixture thus obtained is stirred for an additional few minutes, and the larger lumps of the crystalline sulfochloride are broken up. After removing excess ice, the precipitate is filtered under suction, washed with distilled water, and pressed dry. The crude, reddish sulfochloride thus obtained is taken up in 4000 ml. of methylene chloride and the solution is dried with anhydrous magnesium sulfate. If the sulfochloride precipitates out as an oil after the decomposition with ice, then the aqueous phase is extracted with methylene chloride, followed by the procedure as described. After the clear methylene chloride phase has been concentrated by evaporation, a reddish oil is obtained which is freed from residual solvent with a water jet pump and is then placed in an icebox (−20°). 2,5-dichlorothiphene-3-sulfonic acid chloride is obtained in the form of compact crystals, which can be used without additional purification in the next stage. After recrystallization from petroleum ether, the product has a melting point of 25°–27°.

3500 ml. of absolute chloroform are placed in a 4 liter volume flask and 533 g. of 2,5-dichlorothiophene-3-sulfonic acid chloride are dissolved therein. Dry methylamine is passed in at 20° with stirring until the solution gives a basic reaction with moistened indicator paper. The solution is stirred for an additional 1½ hours at room temperature, then extracted several times with 0.5 N HCl in a separating funnel, dried with anhydrous sodium sulfate, and finally concentrated by evaporation in vacuo. The oil thus obtained is placed in a low temperature container, where it crystallizes. The product thus obtained is purified by recrystallization from 1500 ml. of carbon tetrachloride, is dried in a vacuum drying cabinet at 40° and 2,5-dichlorothiophene-3-sulfonic acid methylamide having a melting point of 59°–61° is obtained.

250 g. of 2,5-dichlorothiophene-3-sulfonic acid methylamide are dissolved in 1500 ml. of absolute ether in a 4 liter volume flask, the apparatus is flushed with dry nitrogen, and a solution of 2.54 mole of n-butyl lithium in 2200 ml. of ether is added slowly dropwise within 1 hour with stirring and continuing to flush with nitrogen. The solution heats up to boiling and a white precipitate settles out, which gradually assumes a grey coloration. The solution is boiled under reflux for 5 hours after the end of the addition of butyl lithium, and after cooling to about 25° dry carbon dioxide is passed into the suspension for ½ an hour, while continuing to stir. The suspension is then poured onto 2000 ml. of water and concentrated hydrochloric acid is added until the aqueous phase gives a strongly acid reaction. The ethereal phase, which contains the starting product and end product, is now separated in a separating funnel and the aqueous phase is additionally extracted with ether. The combined ether phases are extracted three times, each time with 300 ml. of 5% sodium bicarbonate solution. The combined sodium bicarbonate phases are acidified with concentrated hydrochloric acid (pH 1–2) and extracted with 4000 ml. of ether. The ether phase is dried with anhydrous magnesium sulfate and concentrated by evaporation. The crude, pale yellowish carboxylic acid then immediately crystallizes. The product obtained is purified by recrystallization from glacial acetic acid, and 5-chloro-3-methylsulfamoylthiophene-2-carboxylic acid is obtained.

1500 ml. of absolute chloroform are placed in a 4 liter volume flask and 90 g. of finely powdered 5-chloro-3-methylsulfamoylthiophene-2-carboxylic acid is suspended therein while stirring. 85.17 g. of phosphorus pentachloride are then added and the solution is heated to 35°. After about 15 minutes a clear solution is formed. Higher temperatures must be avoided at all costs since otherwise the starting product undergoes ring closure. After a total stirring time of 20–30 minutes, heating is discontinued, a dropping funnel is connected, and 250 ml. of absolute methanol is added dropwise to the solution. After all the methanol has been added the solution is boiled under reflux for 10 minutes and then allowed to cool. The chloroform phase is extracted several times in a separating funnel with a small amount of sodium bicarbonate solution (5%), washed with water, dried with anhydrous sodium sulfate, and then concentrated by evaporation in vacuo. On triturating the oil obtained, the latter crystallizes. The crude product obtained is purified by recrystallization from methanol, and methyl 5-chloro-3-methylsulfamoylthiophene-2-carboxylate having a melting point of 103°–104° is obtained.

9.7 g. of a 55% sodium hydride suspension in mineral oil is washed with absolute benzene in a glass suction filter, and suspended in 70 ml. of absolute dimethylformamide in a 1 liter volume flask under a nitrogen atmosphere. 60 g. of methyl 5-chloro-3-methylsulfamoylthiophene-2-carboxylate dissolved in 525 ml. of absolute dimethylformamide are then added dropwise within 1 hour at 0°, while stirring. The mixture is next stirred for 20 minutes and a solution of 44.5 g. of methyl iodoacetate in 65 ml. of absolute dimethylformamide is then added dropwise within 2 hours at 0°–5°, while cooling. The solution is now stirred at room temperature until a moistened indicator paper gives a neutral reaction. The dimethylformamide is then distilled in vacuo (approximately 1 mm) and the residue is distributed between 400 ml. of 0.5 N hydrochloric acid and 400 ml. of methylene chloride. The methylene chloride phase is separated in a separating funnel, the aqueous phase is extracted with a small amount of methylene chloride, and the combined organic phases are extracted twice by shaking with 150 ml. of 5% sodium bicarbonate solution. The methylene chloride phase is then dried with anhydrous sodium sulfate and concentrated by evaporation in vacuo. A crystalline residue is thus obtained, which is purified by recrystallization from methanol, and methyl 5-chloro-3-(N-methoxycarbonyl-N-methyl)-sulfamoylthiophene-2-carboxylate having a melting point of 103°–104° is obtained.

170 ml. of absolute methanol are placed in a 0.5 liter volume flask and the latter is flushed with dry nitrogen. 3.53 g. of sodium are then added in portions, while stirring. When the sodium has completely dissolved, the mixture is cooled to approximately 30° and 50 g. of methyl 5-chloro-3-(N-methoxycarbonyl-N-methyl)sulfamoylthiophene-2-carboxylate is then added with stirring. The suspension is stirred for 15 minutes at 30° and then carefully heated to the boil. A clear, orange solution thus forms. Boiling is continued until all the starting material has reacted, as shown by thin layer chromatography (about 25–35 minutes). After the solution has cooled to about 45°, it is poured onto 200 g. of ice/300 ml. of 2 N hydrochloric acid, and the desired product precipitates. The aqueous suspension formed is extracted several times by shaking with 2×400 ml. of methylene chloride in a separating funnel. The combined methylene chloride phases are extracted with 2×150 ml. of 10% sodium acetate solution and then extracted by shaking with 3×100 ml. of 10% sodium carbonate solution. The combined sodium carbonate phases are washed with a small amount of methylene chloride and acidified with concentrated hydrochloric acid to a pH of 1–2, while stirring vigorously. The aqueous phase, containing the precipitated end product, is extracted with 2×500 ml. of methylene chloride. The combined methylene chloride phases are dried with sodium sulfate and concentrated by evaporation in vacuo. 6-chloro-4-hydroxy-2-methyl-3-methoxycarbonyl-2H-thieno[2,3e]1,2-thiazine-1,1-dioxide is obtained as yellow, granular crystals which, after digestion in a small amount of cold methanol, suction filtration and drying in a vacuum drying cabinet at 70°, are sufficiently pure for the further reaction. A small amount is recrystallized from benzene for the element analysis, and has a melting point of 200°–203° (with decomposition).

1200 ml. of absolute xylene are placed in a 2 liter volume flask and 11 g. of 6-chloro-4-hydroxy-2-methyl-3-methoxycarbonyl-2H-thieno[2,3-e]-1,2-thiazine-1,1-dioxide are added while stirring. 4.42 g. of 2-aminopyridine are next added and the solution is then boiled under reflux until all the starting product has been shown by thin layer chromatography to have reacted (about 4 hours). A gentle stream of nitrogen is passed through the mixture during boiling under reflux, in order to entrain the methanol that is formed. After the end of the reaction, the solution is cooled to about 120°, activated charcoal is added, and the solution is boiled for an additional short time. A hot water funnel is filled with glycerol and preheated to 120°, and the hot reaction solution at 120° is then filtered through this funnel. When the temperature of the solution has fallen to 70°, the solution is then scratched, whereupon small orange crystals begin to separate out. When cold, the solution is kept for 12 hours in an icebox (−5°) and the precipitate that has separated out is filtered under suction and washed with xylene. The product is dried in vacuo (1 mm, 120°, 2 hours). The orange to yellow crystals thus obtained are 6-chloro-4-hydroxy-2-methyl-3-(2-pyridylcarbamoyl)-2H-thieno[2,3-e]-1,2-thiazine-1,1-dioxide with a melting point of 225°–230° (with decomposition).

EXAMPLE 9

Preparation of 6-bromo-4-hydroxy-2-methyl-3-(2-pyridylcarbamoyl)-2H-thieno[2,3-e]-1,2-thiazine-1,1-dioxide 268.5 g. of finely powdered sodium 2,5-dibromothiophene-3-sulfonate are suspended in 400 ml. of phosphorus oxychloride, 171 g. of phosphorus pentachloride are added, and the reaction solution is heated for 2½ hours at 90°. The solution is then strongly concentrated by evaporation in vacuo, and the residue is poured onto 600 g. of ice. The product is extracted with 3×250 ml. of chloroform, and the organic phase is washed with 2×100 ml. of water, dried, and concentrated by evaporation. The remaining dark oil consisting of 2,5-dibromothiophene-3-sulfonic acid chloride is sufficiently pure for the further reaction.

150 g. of 2,5-dibromothiophene-3-sulfonic acid chloride are dissolved in 500 ml. of absolute chloroform. Dry methylamine is passed into the solution at 20°–25° until moist pH paper gives a basic reaction with the solution. After stirring for an additional hour, the reaction mixture is extracted several times with 0.5 N hydrochloric acid, washed with water, and the organic phase is dried over sodium sulfate. After concentrating the organic phase by evaporation in vacuo, a crystalline residue remains which is digested with a small amount of diisopropyl ether, and N-methyl-2,5-dibromothiophene-3-sulfonamide having a melting point of 100°–104° is obtained.

A solution of N-butyl lithium prepared from 223 ml. of ether, 24.3 g. of N-butyl bromide and 4.4 g. of lithium, is added dropwise at room temperature to a solution of 33.5 g. of N-methyl-2,5-dibromothiophene-3-sulfonamide in 520 ml. of absolute ether. The solution is stirred for an additional 2 hours at room temperature and then dry carbon dioxide is passed in. The reaction mixture is poured onto water, the ether phase is separated, the aqueous phase is acidified with hydrochloric acid, and the product is extracted with ether. After concentrating the dried ether phase by evaporation, a crystalline product remains which is digested with benzene, and 5-bromo-3-N-methylsulfamoylthiophene-2-carboxylic acid having a melting point of 165°–185° is obtained.

30.0 g. of 5-bromo-3-N-methylsulfamoylthiophene-2-carboxylic acid are suspended in 400 ml. of absolute chloroform and 24.2 g. of phosphorus pentachloride is added at 5°–10°, while cooling. As soon as a clear solution has formed, the latter is stirred for an additional 20 minutes at 10° and 100 ml. of absolute methanol is then added dropwise. The solution is boiled under reflux for 10 minutes, and is then extracted with sodium bicarbonate solution, dried, and concentrated by evaporation. The remaining oil is triturated with methanol and methyl 5-bromo-3-N-methylsulfamoylthiophene-2-carboxylate having a melting point of 114°–117° is obtained.

A solution of 31.4 g. of methyl 5-bromo-3-N-methylsulfamoylthiophene-2-carboxylate in 160 ml. of absolute dimethylformamide is added dropwise at 0° to a suspension of 2.52 g. of sodium hydride in 12 ml. of absolute dimethylformamide. The reaction solution is stirred for an additional hour at 0°–2°, a solution of 16.1 g. of methyl bromoacetate in 20 ml. of absolute dimethylformamide is then added dropwise at 0°–5°, and the reaction solution is stirred for an additional 3 hours at room temperature. The reaction solution is concentrated by evaporation in vacuo, the residue is distributed between methylene chloride and 2 N hydrochloric acid, and the organic phase is separated, washed with bicarbonate solution and water, dried, and concentrated by evaporation. The crystalline residue is digested with a small amount of carbon tetrachloride and methyl 5-bromo-3-(N-methoxycarbonylmethyl-N-methyl)sulfamoylthiophene-2-carboxylate having a melting point of 98°–101° is obtained.

3.86 g. of methyl 5-bromo-3-(N-methoxycarbonylmethyl-N-methyl)-sulfamoylthiophene-2-carboxylate is added in portions to 15 ml. of a methanolic solution of 0.01 mole sodium methylate while stirring, and the resulting solution is stirred for 15 minutes at room temperature and then heated under reflux for 20 minutes. The solution is poured onto ice and 2 N hydrochloric acid and the product is extracted with methylene chloride. The organic phase is washed with 10% sodium acetate solution and then extracted with 10% sodium carbonate solution. The sodium carbonate solution is acidified with hydrochloric acid and the precipitated product is extracted by shaking with methylene chloride. After the dried organic phase has been concentrated by evaporation, a crystalline product is obtained which is digested with a small amount of methanol and 6-bromo-4-hydroxy-2-methyl-3-methoxycarbonyl-2H-thieno[2,3-e]-1,2-thiazine-1,1-dioxide having a melting point of 196°–201° is obtained.

3.54 g. of 6-bromo-4-hydroxy-2-methyl-3-methoxycarbonyl-2H-thieno[2,3-e]-1,2-thiazine-1,1-dioxide are boiled under reflux for 6 hours with 1.42 g. of 2-aminopyridine in 150 ml. of absolute xylene. The reaction mixture is allowed to cool to room temperature. The precipitated crude product is recrystallized from dioxane and 6-bromo-4-hydroxy-2-methyl-3-(2-pyridylcarbamoyl)-2H-thieno[2,3-e]-1,2-thiazine-1,1-dioxide having a melting point of 232°–235° is obtained.

EXAMPLE 10

Preparation of 7-chloro-4-hydroxy-2-methyl-3-(2-pyridylcarbamoyl)-2H-thieno[3,4-e]1,2-thiazine-1,1-dioxide 40 g. of methyl 4-acetylamino-3-thiophene carboxylate are dissolved in 1 liter of absolute chloroform, and a solution of 27 g. of sulfuryl chloride in 100 ml. of absolute chloroform is then added dropwise within 20 minutes. The reaction solution is then boiled under reflux for 1 hour. The brownish colored solution obtained is cooled and when its temperature is 10°, 1 liter of ice water is added. The organic solution is then washed with 200 ml. of 5% sodium bicarbonate solution, dried over sodium sulfate, and evaporated to dryness in vacuo. The oily residue is triturated with 100 ml. of ether, whereupon crystallization takes place. The product is suction filtered and recrystallized from ethyl acetate, and methyl 4-acetylamino-5-chloro-3-thiophene carboxylate having a melting point of 119°–121° is obtained. The ethereal filtrate and the mother liquor from the ethyl acetate recrystallization are combined, evaporated to dryness, and the oil that remains is chromatographed on 300 g. of silica gel using methylene chloride/ethyl acetate (4:1) as eluent. An additional portion of methyl 4-acetylamino-5-chloro-3-thiophene carboxylate having a melting point of 119°–121° is obtained.

35 g. of methyl 4-acetylamino-5-chloro-3-thiophene carboxylate are boiled under reflux for 30 minutes with 350 ml. of 5 N solution of hydrochloric acid in absolute methanol. The dark colored solution is then treated in the usual manner with activated charcoal, filtered, and evaporated to dryness in vacuo. The crystalline residue is now dissolved in 180 ml. of absolute methanol at room temperature, and 1400 ml. of absolute ether is added in portions, while constantly stirring, to the obtained solution. After cooling for 30 minutes in an ice bath, the almost colorless product that has crystallized out is suction filtered, washed with ether, and dried in air for 1 hour, and methyl 4-amino-5-chloro-3-thiophene carboxylate hydrochloride, which decomposes between 120° and 140°, is obtained. This hydrochloride can be used without further purification for the next stage.

22.8 g. of methyl 4-amino-5-chloro-3-thiophene carboxylate hydrochloride are suspended in 100 ml. of 36% hydrochloric acid. A solution of 7.25 g. of sodium nitrite in 20 ml. of water is then added dropwise under the surface of the reaction mixture within 10 minutes and at −10°. The reaction mixture is allowed to react for an additional 30 minutes at −10°, and a mixture prepared immediately beforehand from 150 ml. of a 30% solution of sulfur dioxide in glacial acetic acid and a solution of 7.5 g. of cupric chloride in 10 ml. of water is added. The mixture is stirred for an additional hour at 0°–5° and for 3 hours at room temperature, and is then poured into 2 l. of ice water. The product that crystallizes out is suction filtered and dissolved in 800 ml. of toluene. The toluene solution is washed with water, with a sodium bicarbonate solution, and finally washed again with water. After drying over sodium sulfate and concentration by evaporation under reduced pressure, the oil that remains is triturated with a small amount of hexane and allowed to stand overnight in an icebox. 3-carbomethoxy-5-chloro-thiophene-4-sulfochloride is obtained in the form of almost colorless crystals, of melting point 65°–67°. Recrystallization from hexane raises the melting point to 67°–68°.

7.5 g. of glycinemethylester hydrochloride are added in portions at 10°–15° and within 5 minutes to a solution of 16.5 g. of 3-carbomethoxy-5-chlorothiophene-4-sulfochloride in 300 ml. of absolute pyridine. The reaction mixture is then stirred for 4 hours at 25° and evaporated to dryness in vacuo. The residue is dissolved in methylene chloride and the solution is extracted by shaking with ice-cold 2 N hydrochloric acid. The organic phase is dried over sodium sulfate, concentrated by evaporation in vacuo, and the remaining oil is chromatographed on 350 g. of silica gel using methylene chloride/ethyl acetate (4:1) as eluent. The homogeneous fractions are combined, concentrated by evaporation, and the residue is recrystallized from methylene chloride/hexane, and N-(3-carbomethoxy-5-chlorothiophene-4-sulfonyl)-glycinemethylester having a melting point of 68°–70° is obtained.

A solution of 1.15 g. of sodium in 24 ml. of methanol is evaporated to dryness in vacuo and then in a high vacuum, and 240 ml. of absolute toluene is poured over the residue. 8.2 g. of N-(3-carbomethoxy-5-chlorothiophene-4-sulfonyl)glycinemethylester are then added and the reaction mixture is stirred for 4 hours at 60°. The reaction mixture is then cooled to 0° and poured onto 240 ml. of ice-cold 2 N hydrochloric acid, while stirring. The precipitate thus formed is suction filtered, washed with water until neutral, and dried in vacuo at 60°. The product obtained is digested with 30 ml. of methanol, refiltered under suction, and dried, and 3-carbomethoxy-7-chloro-4-hydroxy-2H-thieno[3,4-e]1,2-thiazine-1,1-dioxide, which melts between 230° and 235° with decomposition, is obtained.

A solution of 2.93 g. of 3-carbomethoxy-7-chloro-4-hydroxy-2H-thieno[3,4-e]1,2-thiazine-1,1-dioxide in 75 ml. of dimethylformamide is mixed under argon at 10° with 0.022 mole of sodium hydride (1.0 g. of a 55% dispersion in mineral oil), and the resulting solution is then stirred for an additional 4 hours at 25°. 2.5 ml. of methyl iodide is then added dropwise at 10°–15°. The reaction mixture is next stirred for 16 hours at room temperature, poured onto 750 ml. of ice water, and the resultant mixture is acidified with concentrated hydrochloric acid. The precipitate that settles out is suction filtered, dissolved in chloroform, and the solution is dried over sodium sulfate. After the residue has been concentrated by evaporation in vacuo, it is chromatographed on 150 g. of silica gel using chloroform as eluent. After crystallization from acetonitrile, 3-carbomethoxy-7-chloro-4-hydroxy-2-methyl-2H-thieno[3,4-e]1,2-thiazine-1,1-dioxide having a melting point of 188°–191° is obtained.

A mixture of 2.2 g. of 3-carbomethoxy-7-chloro-4-hydroxy-2-methyl-2H-thieno-[3,4-e]-1,2-thiazine-1,1-dioxide, 0.9 g. of 2-aminopyridine and 240 ml. of absolute o-xylene is boiled under reflux for 7 hours while stirring, approximately 80 ml. of the o-xylene being slowly distilled during the first 2 hours. After the reaction mixture has been cooled to room temperature, it is concentrated to approximately 60 ml. by evaporation in vacuo and cooled in an ice bath. The product that crystallizes out is suction filtered, washed with ether, dried and recrystallized from acetonitrile, and 7-chloro-4-hydroxy-2-methyl-3-(2-pyridylcarbamoyl)-2H-thieno[3,4-e]-1,2-thiazine-1,1-dioxide having a melting point of 218°–220° (with decomposition) is obtained.

EXAMPLE A

Suppositories of the following composition are prepared in accordance with known procedures:

| | |
|---|---|
| 6-chloro-4-hydroxy-2-methyl-3-(2-pyridyl-carbamoyl)-2H-thieno[2,3-e]-1,2-thiazine-1,1-dioxide | 0.005 g. |
| Hydrogenated coconut oil | 1.250 g. |
| Carnauba wax | 0.045 g. |

EXAMPLE B

Tablets of the following composition are prepared in accordance with known procedures:

| | Per Tablet |
|---|---|
| 6-chloro-4-hydroxy-2-methyl-3-(2-pyridyl-carbamyl)-2H-thieno[2,3-e]-1,2-thiazine-1,1-dioxide | 5.00 mg. |
| Lactose | 84.50 mg. |
| Maize starch | 10.00 mg. |
| Magnesium stearate | 0.50 mg. |

EXAMPLE C

Capsules of the following composition are prepared in accordance with known procedures:

| | Per Capsule |
|---|---|
| 6-chloro-4-hydroxy-2-methyl-3-(2-pyridyl-carbamoyl)-2H-thieno[2,3-e]-1,2-thiazine-1,1-dioxide | 10 mg. |
| Lactose | 165 mg. |
| Maize starch | 30 mg. |
| Talc | 5 mg. |
| Total Weight | 210 mg. |

We claim:
1. A compound of the formula

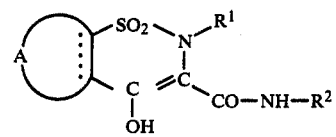

wherein A together with the two carbon atoms forms the group

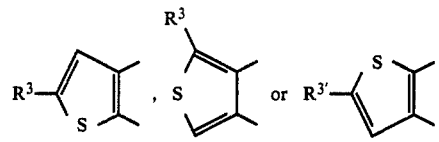

and the dotted line indicates the double bond present in the first and last thieno structures above, $R^1$ is lower alkyl, $R^2$ is selected from the group consisting of 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazine-3-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6-dimethyl-2-pyridyl, 5-isoxazolyl, 5-methyl-3-isoxazolyl, 3,4-dimethyl-5-isoxazolyl, 2,6-dimethyl-4-pyrimidinyl, 1,2,3,4-tetrazol-5-yl or a phenyl radical optionally substituted by halogen, hydroxy, lower alkyl, trifluoromethyl or lower alkoxy, $R^3$ is halogen and $R^{3'}$ is hydrogen or halogen, or a pharmaceutically acceptable salt thereof.

2. A compound in accordance with claim 1, wherein A is the group

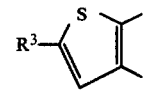

3. A compound in accordance with claim 1, wherein A is the group

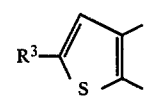

4. A compound in accordance with claim 1, wherein $R^2$ is 2-thiazolyl, 4-methyl-2-thiazolyl, 4,5-dimethyl-2-thiazolyl, 5-methyl-1,3,4-thiadiazolyl, 2-pyrazinyl, 2- pyrimidinyl, 1,2,4-triazine-3-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6-dimethyl-2-pyridyl, 5-isoxazolyl, 5-methyl-3-isoxazolyl, 3,4-dimethyl-5-isoxazolyl, 2,6-dimethyl-4-pyrimidinyl or 1,2,3,4-tetrazol-5-yl.

5. A compound in accordance with claim 1, wherein $R^2$ is 2-pyridyl.

6. A compound in accordance with claim 1, wherein $R^3$ and $R^{3'}$, independently, are chlorine or bromine.

7. A compound in accordance with claim 1, wherein $R^3$ and $R^{3'}$ are chlorine.

8. A compound in accordance with claim 1, wherein $R^1$ is methyl.

9. A compound in accordance with claim 1, 4-hydroxy-2-methyl-3-(2-pyridylcarbamoyl)-2H-thieno[3,2-e]1,2-thiazine-1,1-dioxide.

10. A compound in accordance with claim 1, 4-hydroxy-2-methyl-3-(2-thiazolylcarbamoyl)-2H-thieno[3,2-e]1,2-thiazine-1,1-dioxide.

11. A compound in accordance with claim 1, 4-hydroxy-2-methyl-3-pyrazinylcarbamoyl-2H-thieno[3,2-e]1,2-thiazine-1,1-dioxide.

12. A compound in accordance with claim 1, 4-hydroxy-2-methyl-3-[3-(5-methylisoxazolyl)carbamoyl]-2H-thieno[3,2-e]1,2-thiazine-1,1-dioxide.

13. A compound in accordance with claim 1, 6-chloro-4-hydroxy-2-methyl-3-(2-pyridylcarbamoyl)-2H-thieno[3,2-e]1,2-thiazine-1,1-dioxide.

14. A compound in accordance with claim 1, 6-chloro-4-hydroxy-2-methyl-3-(2-thiazolylcarbamoyl)-2H-thieno[3,2-e]1,2-thiazine-1,1-dioxide.

15. A compound in accordance with claim 1, 6-chloro-4-hydroxy-2-methyl-3-(2-pyridylcarbamoyl)-2H-thieno[2,3-e]1,2-thiazine-1,1-dioxide.

16. A compound in accordance with claim 1, 6-bromo-4-hydroxy-2-methyl-3-(2-pyridylcarbamoyl)-2H-thieno[2,3-e]1,2-thiazine-1,1-dioxide.

17. A compound in accordance with claim 1, 7-chloro-4-hydroxy-2-methyl-3-(2-pyridylcarbamoyl)-2H-thieno[3,4-e]1,2-thiazine-1,1-dioxide.

* * * * *